United States Patent [19]

Tajima

[11] 4,226,792
[45] Oct. 7, 1980

[54] LEAD CHELATE COMPLEX COMPOUNDS

[75] Inventor: Yuji A. Tajima, Teaneck, N.J.

[73] Assignee: NL Industries, Inc., New York, N.Y.

[21] Appl. No.: 350,635

[22] Filed: Mar. 5, 1964

[51] Int. Cl.$^3$ .............................................. C07F 7/24
[52] U.S. Cl. ................................ 260/435 A; 149/24;
 149/98; 260/429 J; 260/435 R
[58] Field of Search ...................... 149/24, 23, 27;
 260/435, 429 J, 242, 435 R, 435 A

[56] References Cited

U.S. PATENT DOCUMENTS

| | | | |
|---|---|---|---|
| 2,021,497 | 1/1935 | Brun | 149/24 X |
| 2,595,798 | 5/1952 | Ligett et al. | 260/242 |
| 2,901,496 | 8/1959 | Cowan | 260/429.2 X |

OTHER PUBLICATIONS

Dywer et al., Chelating Agents and Metal Chelates, Academic Press, New York, 1964, pp. 106, 107, 126, 133, 134 and 137.
Stary, The Solvent Extraction of Metal Chelates, The MacMillan Company, New York, 1964, pp. 107, 108 and 210.
Stone et al., Advances In Organometallic Chemistry, vol. 3, Academic Press, New York, 1965, pp. 440 to 442 and 446.

*Primary Examiner*—Leland A. Sebastian
*Attorney, Agent, or Firm*—Gary M. Nath

EXEMPLARY CLAIM

1. Lead chelate complex compounds selected from the group consisting of lead 3-nitrosalicylaldehyde, lead 5-nitrosalicylaldehyde, lead 5-chlorosalicylaldehyde, lead 2, 4-dihydroxybenzophenone, lead ortho-hydroxyacetophenone, lead 1, 4-dihydroxyanthraquinone, lead 2,5-dihydroxybenzoquinone, lead bis-ortho-hydroxyphenacylphenone, lead phenylsalicylate, lead ethylsalicylate, lead disalicylamide, lead disalicylethylene diamide, lead salicylamide, lead bis-salicylaldehyde-o-phenylene diimine, lead salicylidene acetamide, lead bis-salicylaldehyde-ethylene diimine, and lead (o-carboxyphenyl) salicylaldimine.

18 Claims, 4 Drawing Figures

LEAD CHELATE COMPLEX COMPOUNDS

This invention relates to new chemical compounds useful as ballistic modifiers, and to novel and improved ballistic propellants containing the same. In particular, this invention relates to novel lead chelate complexes useful as ballistic modifiers, and to double-base propellant compositions containing the same.

Ballistic propellant compositions in general have burning properties which are characteristic of the composition of the propellant and of the conditions under which it is burned. In the case of so-called double-base propellants, which are compositions containing nitrocellulose and nitroglycerine, the burning characteristics are directly related to the relative proportions of nirocellulose and nitroglycerine employed, and also to the pressure under which the burning takes place.

For various reasons, it is frequently desirable to modify the burning characteristics of such propellants to achieve properties that cannot be obtained by merely varying the proportions of nitrocellulose and nitroglycerine. For example, it is particularly desirable for many purposes to increase the burning rate of the propellant. Increasing the burning rate causes the energy content of the propellant to be delivered more rapidly than would otherwise be the case, which in turn provides a more rapid initial acceleration of the projectile.

Modifiers which increase the burning rate of the grain also decrease the dependency of the burning rate upon pressure throughout the pressure range in which they are active.

As the pressure is increased, approaching the "active region," in which the burning rate is pressure-independent, the activity of the modifier and consequently the burning rate of the modified propellant, increase with pressure to a point where the activity of the modifier is at a maximum, and the burning rate of the modified propellant substantially exceeds the burning rate of the unmodified propellant at the same pressure. This point corresponds to the beginning of the "active region" as commonly understood by the rocket engineer. In the "active region," the burning rate of the unmodified propellant tends to increase with increasing pressure, but the activity of the modifier decreases with increasing pressure. Throughout the "active region," therefore, such modifiers tend to equalize the burning rate by increasing the burning rate more at lower pressures, where burning of the unmodified grain would normally be relatively slow, and less at the higher pressures where the unmodified grain would be relatively fast. This effect may be seen on a log-log or similar plotting of burning rate versus pressure, where, in the range where the modifier is active, the burning rate-pressure curve becomes flattened out to a more or less horizontal form. At higher and lower pressures, the modifier is not active, and the burning rate-pressure curve ascends in the general manner characteristic of an unmodified propellant. This "plateau effect" was first observed in connection with double-base propellant compositions containing lead stearate, and the initial observation led to an intensive search for modifiers possessing improved properties, particularly low pressure exponent and low temperature coefficient. The term "pressure exponent" refers to the value of n in the equation $$B = KP^n$$

where B is the burning rate of the composition, K is a function of the initial temperature and P is the pressure. The pressure exponent n, which is also sometimes referred to as the combustion index, is therefore a measure of the effect of pressure on burning rate, and a low value of n indicates a small effect of pressure on burning rate in the range under consideration—i.e. a "plateau" effect.

In the case of some modifiers, the effect of pressure on modifier activity is uniform over most of the "active region," but there is a range at the higher pressure end of this region in which the effect of pressure in depressing modifier activity exceeds the effect of pressure in speeding up the burning rate of the unmodified propellant, such that the burning rate of the modified grain actually decreases with increasing pressure. Under these conditions, the value of the combustion index becomes negative. This characteristic is referred to as "mesa" burning, from the characteristic profile of the log B/log P curve, and is advantageous because it stabilizes the burning characteristics of the grain, particularly in cases where, for one reason or another, the pressure tends to exceed the designed strength of the rocket motor case.

One of the best ballistic modifiers heretofore discovered, lead salicylate, imparts "mesa" ballistics to double-base propellants.

Various other lead compounds, as well as compounds of other metals such as copper, cobalt, manganese, tantalum, molybdenum, zinc, aluminum, vanadium, tin, magnesium, silver, chromium, titanium, thorium, cadmium, potassium, bismuth, cerium, iron, nickel and zirconium have been evaluated. Of these, the compounds showing the most promise, and those which have been most extensively used in operational double-base propellant compositions are lead salicylate, and derivatives thereof, admixed with copper salicylate or lead and other salts of aliphatic acids. These include particularly lead salicylate, lead beta-resorcylate, cuprous salicylate, lead stearate and lead 2-ethylhexoate.

The principal drawback of these and other ballistic modifiers heretofore suggested is that the activity (increase in burning rate as compared with the burning rate of the unmodifed grain) decreases as the energy content (heat of emplosion) of the compositiion increases.

This drawback in conventional modifiers, i.e. the decrease in modifier activity associated with increase in heat of explosion, is apparent, for example, in a double-base grain consisting of nitrocellulose, nitroglycerine and triacetin. When incorporated in such a composition, lead salicylate exhibits good modifier activity when the grain composition is formulated to produce a heat of explosion of 825 calories per gram. When the composition is adjusted to produce a heat of explosion of 900 calories per gram, the activity of the modifier is appreciably diminished, and when the composition is formulated to produce an explosion heat of 1000 calories per gram, the activity is completely absent.

Aside from the above considerations, existing ballistic modifiers are, in general, active only at relatively low pressures (below about 2000 psi). Such pressures are customarily employed in rocket propulsion, and are useful in that and other applications where relatively low pressures are experienced. Propellants used in guns, on the other hand, frequently develop much higher pressures, and conventional modifiers are in general inactive in the pressure region exceeding 2000 psi.

Other things being equal, the initial acceleration imparted to a projectile is proportional to the pressure developed, and the advantages already proven for conventional modifiers in rocket propellant compositions would be of equal value in certain gunnery explosives, if there were a modifier active at the high pressures encountered in certain gunnery applications, for example, recoilless rifles and the like.

An object of this invention, therefore, is to provide ballistic modifiers of improved characteristics. Another object is to provide improved ballistic propellant compositions. Another object is to provide ballistic modifiers which are active in high-energy double-base propellants. Still another object is to provide ballistic modifiers that are active both at low pressures and high pressures. A further object is to provide ballistic propellants having low pressure exponents. A still further object is to provide ballistic propellants having low temperature coefficients.

Other objects and advantages will become apparent from the following more complete description and claims.

It has now been discovered that certain lead chelate complexes more fully described below possess outstanding properties as modifiers for ballistic propellants, and impart outstanding ballistic properties to propellant compositions in which they are included.

Broadly, this invention contemplates, as a new class of chemical compounds, the lead chelate complexes of compounds of the general formula

wherein R is a radical containing a replaceable hydrogen atom which is less acidic than the hydrogen atom of a carboxyl group, and $R^1$ is an electron-donating radical.

This invention also contemplates a ballistic propellant composition containing a propellant and a lead chelate complex of a compound having the general formula

wherein R and $R^1$ are groups as defined above.

Examples of the groups useful according to this invention as the R group in the above formulas are the hydroxyl, —OH, sulfhydryl, —SH, and similar groups which are Lewis acids, having a hydrogen atom, providing that such hydrogen atom is less acidic than the hydrogen atom of a carboxyl, —COOH, group.

Examples of groups useful according to this invention as the R' group include a wide variety of electron donating groups, such as aldehyde, ester, ketone, amide, aldoxime, amine, nitro, sulfhydryl, hydroxyalkyl, and the like.

Examples of specific compounds according to the present invention, therefore, include by way of example the lead chelate complexes of: salicylaldehyde and derivatives thereof, such as lead salicylaldehyde, lead 3-nitrosalicylaldehyde, lead 5-nitrosalicylaldehyde, lead 5-chlorosalicylaldehyde, lead 4, 6-dimethylsalicylaldehyde, diphenyl lead salicylaldehyde, lead 3-chlorosalicylaldehyde, lead 5-methylsalicylaldehyde, lead 5-tert-butylsalicylaldehyde, lead 4-methoxysalicylaldehyde, lead 4-hydroxysalicylaldehyde, lead 3-methoxysalicylaldehyde, lead 3,5-dimethylsalicylaldehyde, lead 5-phenylsalicylaldehyde, lead 4-chlorosalicylaldehyde and the like.

Other new and useful compounds according to this invention, possessing ballistic modifier properties, are the lead chelate complexes of orthohydroxy ketones and derivatives thereof, such as: lead 2,4-dihydroxybenzophenone, lead orthohydroxyacetophenone, lead 1,4-dihydroxyanthraquinone, lead 2,5-dihydroxybenzoquinone, lead bis-ortho-hydroxy-phenacylphenone, lead 2-hydroxy-4-methoxybenzophenone and the like.

Additional compounds contemplated within the scope of this invention, both as new and useful compounds in their own right and as useful modifiers for ballistic propellant compositions according to the invention, include lead chelate complexes of esters of salicyclic acid such as lead phenylsalicylate, lead ethylsalicylate and the like, and amides and N-substituted amides of salicylic acid, such as lead disalicylamide, lead disalicylethylene diamide, lead salicylamide and the like.

Also contemplated within the scope of this invention, as new and useful compounds having new and useful properties as modifiers for ballistic propellants, are the lead chelate complexes of Schiff bases and N-substituted Schiff bases of salicylaldehyde. Such compounds include, for example, lead bis-salicylaldehyde-o-phenylene diimine, salicylidene acetamide, lead salicylaldoxime, lead bis-salicylaldehyde-ethylene diimine, lead (o-carboxyphenyl) salicylaldimine, lead N-(2-hydroxyethyl)salicylaldimine and the like.

Additional new and useful compounds contemplated within the scope of this invention, and which have useful ballistic modifier properties when used in ballistic propellant compositions according to this invention include the lead chelate complexes of substituted phenols such as lead o-nitrophenol, lead o-aminophenol and the like, of o-hydroxynaphthaldehydes, such as lead 2-hydroxynapthaldehyde, of substituted naphthols, such as lead o-nitronaphthol, of saligenin, such as lead saligenin, and of disalicylidene acetone, such as lead disalicylidene acetone.

PREPARATION OF LEAD CHELATE COMPLEXES

Figure 3:
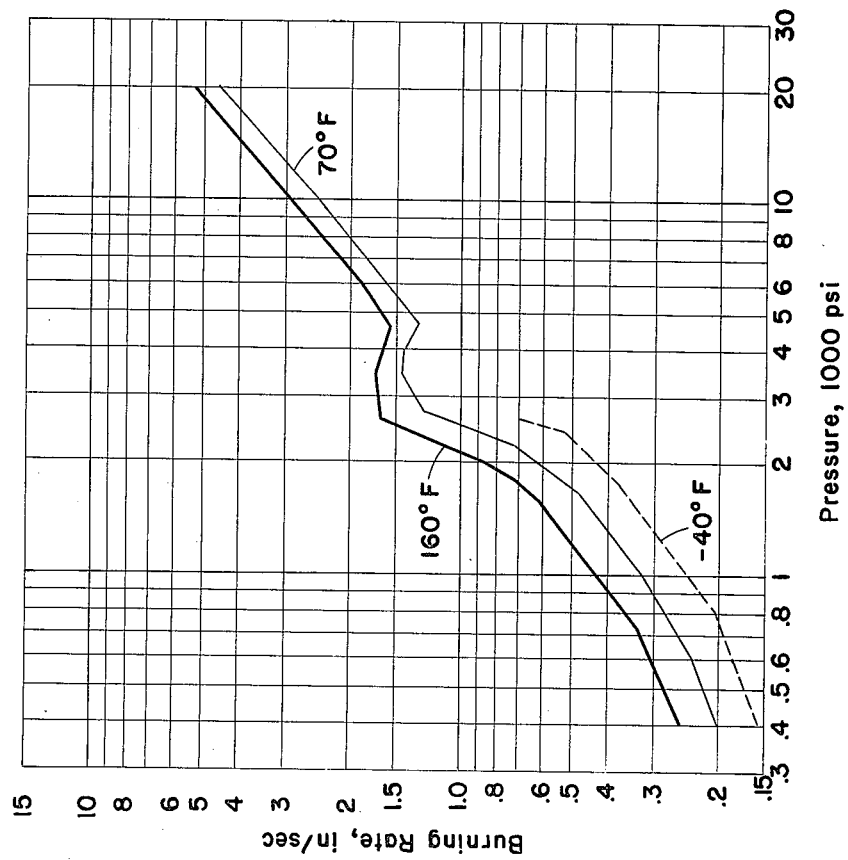
FIGS. 3 and 4 also compare the burning rates of compositions with and without the modifier.

The lead chelate complexes of this invention may be prepared in a variety of ways as will be appreciated by those skilled in the art. Examples of some of the most convenient and efficient preparation methods follow:

EXAMPLE I

PREPARATION OF LEAD SALICYLALDEHYDE

Salicylaldehyde (1 mol) is added to a water slurry of PbO (0.5 mol) with stirring and placed on a steam bath until dry. The mixture is stirred intermittently while drying. After drying, the solid residue is washed with water and then with ethanol, and allowed to air dry.

Lead 3-chlorosalicylaldehyde, lead 5-methylsalicylaldehyde, lead 5-tert-butylsalicylaldehyde, lead 4-methoxysalicylaldehyde, lead 4-hydroxysalicylaldehyde, lead 3,5-dimethylsalicylaldehyde and lead 2-hydroxynaphthaldehyde are prepared according to the same procedure, substituting 1 mol of the appropriate ligand for the 1 mol of salicylaldehyde.

Lead 1,4-dihydroxyanthraquinone is prepared by the same procedure, except that the slurry is made up in a 20% solution of acetone in water, instead of in pure water.

Lead 2,5-dihydroxybenzoquinone is prepared by the same procedure, except that the steam bath is not used, and the slurry is instead allowed to dry in air, because of the sensitivity of the ligand to heat.

Lead disalicylidene acetone is also prepared according to the same procedure. The product is the monolead salt.

EXAMPLE II

PREPARATION OF LEAD 3-NITROSALICYLALDEHYDE

Lead oxide (1 mol) is mixed with water and stirred in a ball mill. Then 3-nitrosalicylaldehyde (2 mols) is added and the mixture ground until the color of the lead oxide has disappeared. The solids are filtered, washed and dried.

Lead 5-nitrosalicyaldehyde, lead 5-chlorosalicylaldehyde, and lead 4,6-dimethylsalicylaldehyde are prepared in the same manner, substituting 2 mols of the appropriate ligand for the 2 mols of 3-nitrosalicylaldehyde.

EXAMPLE III

PREPARATION OF DIPHENYL LEAD SALICYLALDEHYDE

Diphenyl lead dichloride (0.01 mol) is mixed with 0.02 mol of sodium salicylaldehyde in acetone. The solution is allowed to stand 10 minutes and then filtered. Water is added to the filtrate to precipitate the lead chelate complex, which is then separated by filtration.

EXAMPLE IV

PREPARATION OF LEAD 4-CHLOROSALICYLAIDEHYDE

Lead 4-chlorosalicylaldehyde is prepared by the double decomposition of the sodium salt of the ligand and lead acetate trihydrate.

4-chlorosalicylaldehyde (0.250 mols) is placed in a solution of NaOH (0.2 mols) and 0.1 mol of lead acetate trihydrate, $Pb(OAc)_2 \cdot 3H_2O$, are added quickly. The lead chelate complex is formed as a solid, and is separated by filtration, followed by thorough washing with water and ethanol.

Lead 4-chlorosalicylaldehyde, lead 2-hydroxy-4-methoxybenzophenone, lead disalicylamide, lead disalicylethylene diamide, lead salicylamide, lead bis-salicylaldehyde-o-phenylene diimine, lead salicylaldoxime, lead bis-salicylaldehyde-ethylene diimine, lead (o-carboxyphenyl) salicylaldimine, and lead N-(2-hydroxyethyl)-salicylaldimine are prepared by the same procedure, substituting equivalent quantities of the appropriate ligands for the 4-chlorosalicylaldehyde, i.e. 0.250 or 0.125 mols as the case may be.

EXAMPLE V

PREPARATION OF LEAD 3-METHOXYSALICYLALDEHYDE 3-methoxysalicylaldehyde (1 mol) is placed in a ball mill with litharge PbO, (0.05 mol) in 95% ethanol. The mixture is milled until the yellow color of the litharge disappears. The solids are washed with water and alcohol, then air-dried at room temperature.

Lead 5-phenylsalicylaldehyde, lead 2,4-dihydroxybenzophenone, lead o-hydroxyacetophenone, lead bis-o-hydroxyphenacylphenone, lead phenylsalicylate, lead ethylsalicylte, lead o-nitrophenol, lead o-aminophenol, lead o-nitronaphthol and lead saligenin (which forms a mono lead salt), are prepared by the same procedure, substituting 1 mol of the appropriate ligand for the 1 mol of 3-methoxysalicylaldehyde.

EXAMPLE VI

PREPARATION OF LEAD SALICYLIDENE ACETAMIDE

Salicylidene acetamide (0.1 mol) is placed in a Stark extractor with benzene and litharge, PbO (1 mol).

The benzene is refluxed until the theoretical amount of water is azeotroped. The solids are filtered, washed with water and with ethanol, and air dried.

Most of the ligands used in the preparation of the compounds of this invention are commercially available from laboratory supply houses and chemical manufacturers. The remainder may be readily prepared according to standard laboratory procedures. The procedures used for preparation of some of the ligands are given as follows:

PREPARATION OF 3-NITROSALICYLAIDEHYDE

Salicylaldehyde (10 grams) is dissolved in acetic acid (50 grams) and nitrated with 10 ml. of red fuming nitric acid at 40°–45° C. The mixture is poured over ice and filtered. The solid product is a mixture of 3- and 5-nitrosalicylaldehyde. The isomers are separated by fractional recrystallization in acetic acid or by fractional recrystallization of their sodium salts in warm water, the 5-nitro isomer being less soluble in water than the 3-nitro isomer.

PREPARATION OF 4,6-DIMETHYL SALICYLAIDEHYDE 4,6-dimethyl salicylaldehyde is prepared by a Reimar-Tieman reaction on 3,5 -dimethyl phenol, as described in Vogel, "Practical Organic Chemistry," page 672. The same method is used to prepare 3-chlorosalicylaldehyde (together with an isomer from which it is separated by chromatography), 5-methylsalicylaldehyde, and 5-phenylsalicylaldehyde.

PREPARATION OF DIPHENYL LEAD DICHLORIDE

Diphenyl lead dichloride is prepared by the procedure described by Heap, Saunders and Stacey in the Journal of the Chemical Society, 1949, page 919.

PREPARATION OF 4-METHOXY SALICYLAIDEHYDE

Beta-resorcyl aldehyde (13.8 grams) is dissolved in sodium methoxide (in amount equivalent to 2.3 grams of sodium), and 14.2 grams of methyl iodide are added.

The mixture is refluxed for 4 hours. Alcohol (methanol) is distilled off and dilute HCl added. The resulting red liquid is separated from the aqueous layer, dried and steam distilled.

PREPARATION OF 5-TERT-BUTYL SALICYLALDEHYDE 5-tert-butyl salicylaldehyde is prepared by a Duff reaction on p-tert-butyl phenol, according to the procedure described in Journal of the Chemical Society 46, page 1512 (1951). The same procedure is used to prepare 3, 5-dimethyl salicylaldehyde.

PREPARATION OF 4-CHLOROSALICYLALDEHYDE 4-chlorosalicylaldehyde is prepared by the procedure described by Hodgson and Jenkinson in Journal of the Chemical Society, 1927, pages 1740-1742.

PREPARATION OF DISALICYLAMIDE

Disalicylamide is prepared as described by J. Mc Connors in Journal of the Chemical Society 91, page 196 (1907).

PREPARATION OF BIS-O-HYDROXYPHENACYLPHENONE

Bis-o-hydroxyphenacylphenone is prepared as described in Chemical Abstracts 37, page 2358 (1943).

PREPARATION OF DISALICYLETHYLENE DIAMIDE

Ethyl salicylate (16.6 grams) is mixed with 6.0 grams of ethylene diamine and allowed to stand. The mixture is shaken with 40 cc. of 6 N.HCl. A white solid precipitates, which is filtered and washed with dilute HCl and with water. To recover further amounts of product, the washings are cooled in ice and filtered again.

PREPARATION OF BIS-SALICYLALDEHYDE-O-PHENYLENE DIIMINE

Salicylaldehyde (12.2 grams) is mixed with o-phenylene diamine (5.4 grams) in benzene and placed in a Stark reactor until 2 ml. of $H_2O$ are azeotroped. The benzene solution is cooled and heptane is added to precipitate the solid product.

Bis-salicylaldehyde-ethylene diimine is prepared by the same procedure, substituting an equivalent quantity of ethylene diamine for the o-phenylene diamine. The same procedure is also used to prepare N(2-hydroxyethyl)-salicylaldiimine, using an equivalent quantity of ethanol amine in place of the o-phenylene diamine.

PREPARATION OF (O-CARBOXYPHENYL)SALICYLALDIIMINE

Anthranilic acid (1 mol) is dissolved in ethanol and 1 mol of salicylaldehyde is added with stirring. The product separates as an orange solid which is filtered out and washed with ethanol.

Double-base propellant compositions employing the ballistic modifiers of this invention are prepared according to conventional procedures by blending nitrocellulose, nitroglycerine, stabilizer and inert plasticizer in proportions to give an extrudable consistency coupled with the desired energy content (heat of explosion). The modifier is incorporated into the blend at any convenient stage of manufacture in amount depending somewhat on the nature of the particular modifier, but principally on the ballistic properties desired. In general, the modifying action of the ballistic modifier increases with increasing concentration of the modifier in the double-base composition. However, the optimum amount that can be incorporated in a given composition is determined by other specifications required for practical utilization of the double-base grain; viz., need for nitrocellulose binder, nitroglycerine (explosive plasticizer), inert plasticizer and stabilizer. The relative proportions of these ingredients determine the heat of explosion, burning rate, storage stability and physical properties such as tensile strength and the like.

EXAMPLE VII

A double-base propellant composition was prepared according to the following formulation:

|  | % (Wt.) |
|---|---|
| Nitrocellulose (12.6% N) | 52.0 |
| Nitroglycerine | 27.5 |
| Dinitrotoluene | 9.3 |
| Triacetin | 7.2 |
| 2-Nitrodiphenylamine | 2.0 |
| Lead salicyaldehyde | 2.0 |
|  | 100.0 |

Figure 1:
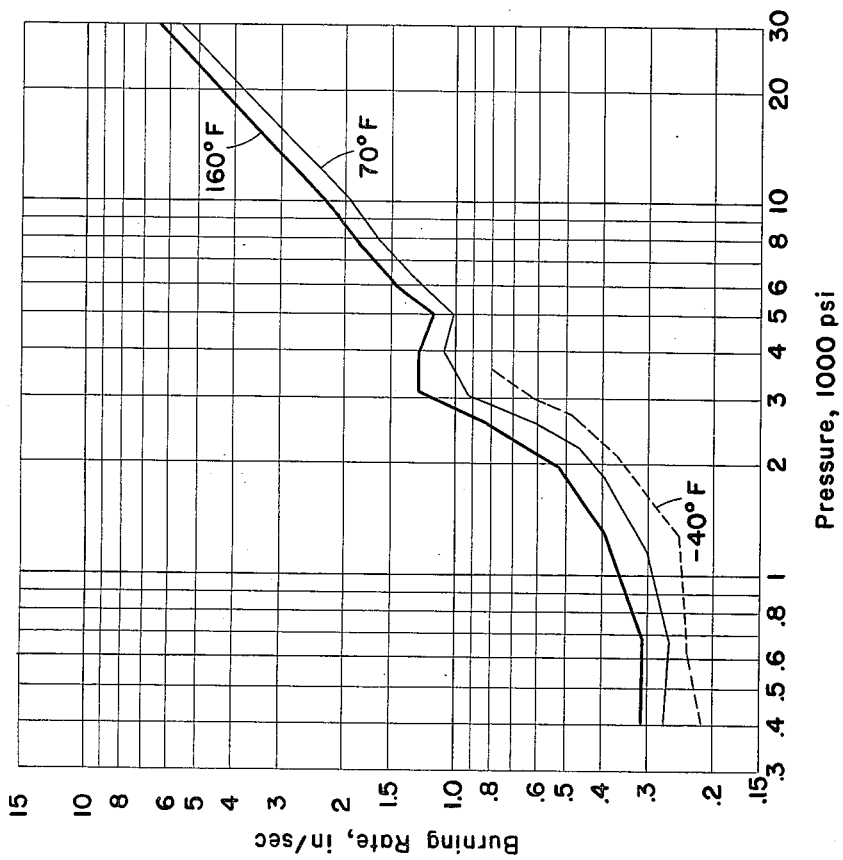
FIGS. 1 and 2 compare the burning rates of compositions with and without the modifier.

The experimentally-determined heat of explosion for the above composition was 864 calories per gram, which agreed well with the calculated value of 829 cal./gm. The burning rate of this composition was determined according to conventional procedures, using strands prepared as described in "Direct Determination of Burning Rates of Propellant Powders," Crawford, Huggett, Daniels and Wilfong, Analytical Chemistry 19, September, 1947, and in "Standard Methods and Procedures for the Strand Burning-Rate Evaluation of Rocket Propellant Powder," Washington, Buord 29 May, 1953 (NAVORD OD 9376). The burning rate was determined over a series of pressures for each of three different temperatures. The results of these determinations are shown graphically in FIG. 1, which clearly shows an increase in burning rate as the pressure increases, up to a pressure of about 3000 psi, followed by a levelling-off at about one inch per second until the pressure reached 5000 psi, after which the burning rate again started to increase with increasing pressure.

Figure 2:
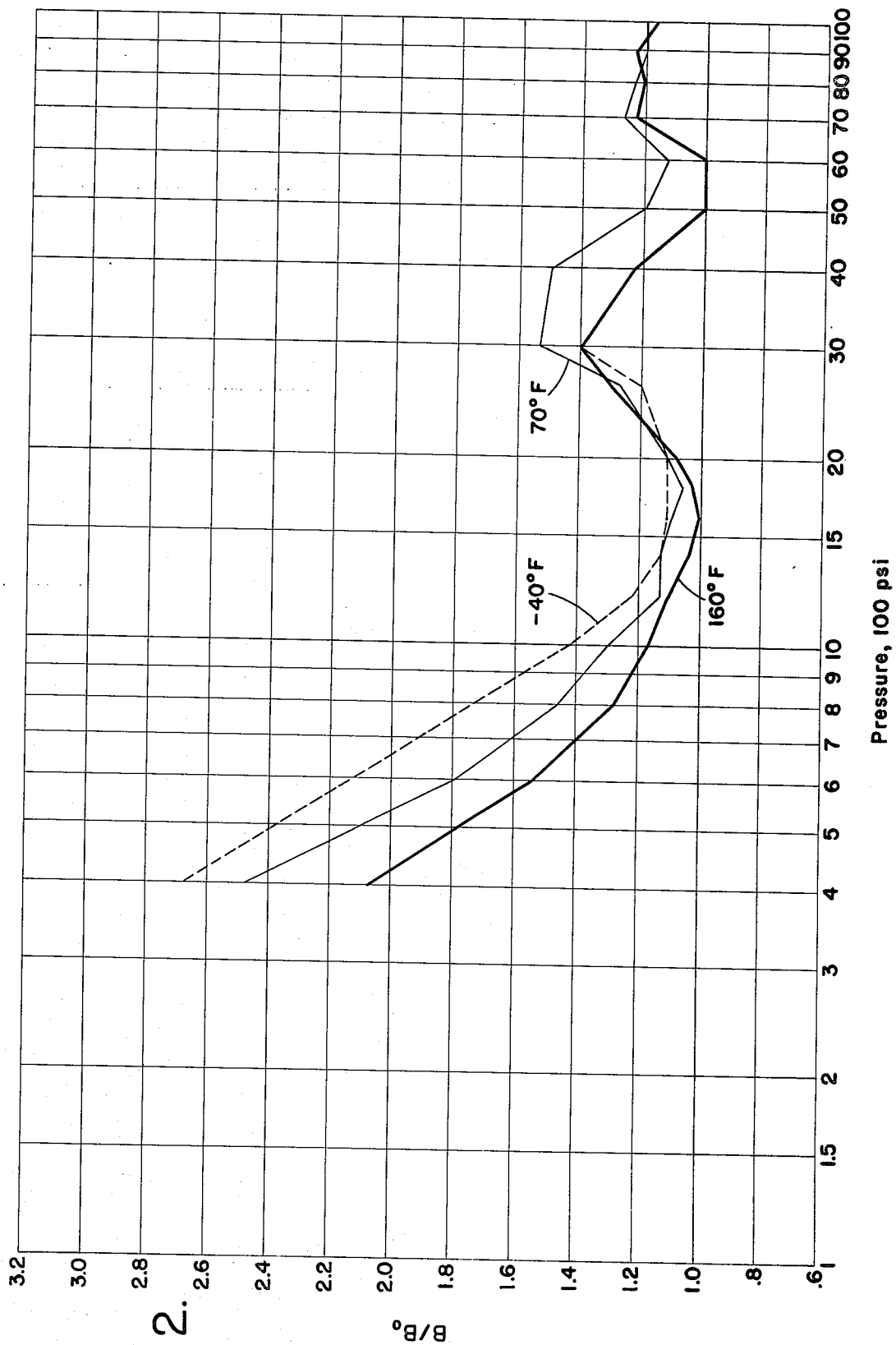

For the purposes of comparison, a similar composition was prepared, but omitting the modifier (lead salicylaldehyde), and the burning rate was similarly tested over a range of pressures for each of three different starting temperatures. The results of these determinations are shown graphically in FIG. 2, which is a plot of modifier activity (B/Bo) against pressure. The expression "B/Bo" is defined as the burning rate of the modified strand divided by that of the unmodified strand. Hence, any value of B/Bo in excess of 1 denotes an increase in burning rate. In FIG. 2, it is seen that the modifier is active in two distinct pressure regions; it is exceedingly active in the low-pressure region between about 400 and 1000 psi, becomes less active in the region between 1000 and 2000 psi, increases again to a definite peak in the range between 3000 and 4000 psi, and becomes again less active at higher pressures. This correlates with the results depicted in FIG. 1, and shows, in particular, that in the 3000-5000 psi range, as the modifier activity B/Bo decreases, it effects the normal tendency for burning rate to increase with pressure so that in this range the burning rate is largely independent of the pressure.

EXAMPLE VIII

A double-base propellant composition was prepared according to the following formulation:

|  | % (Wt.) |
|---|---|
| Nitrocellulose (12.6% N) | 48.0 |
| Nitroglycerine | 38.3 |
| Dinitrotoluene | 3.0 |
| Triacetin | 6.7 |
| 2-Nitrodiphenylamine | 2.0 |
| Lead salicylaldehyde | 2.0 |
|  | 100.0 |

The heat of explosion of this composition was calculated to be 996 calories per gram, which agrees exceedingly well with the observed value of 998 cal./gm.

The burning rate was determined as in Example VII, over a series of pressures at each of three temperatures. The results of these determinations are shown graphically in FIG. 3. As shown in FIG. 3, the burning rate increases rapidly with pressure up to a pressure of about 2,500 psi, at which point the burning rate levels off in the neighborhood of 1.5 inches per second throughout the range between 2,500 and 5,000 psi, and then continues to increase with increasing pressure.

Figure 4:
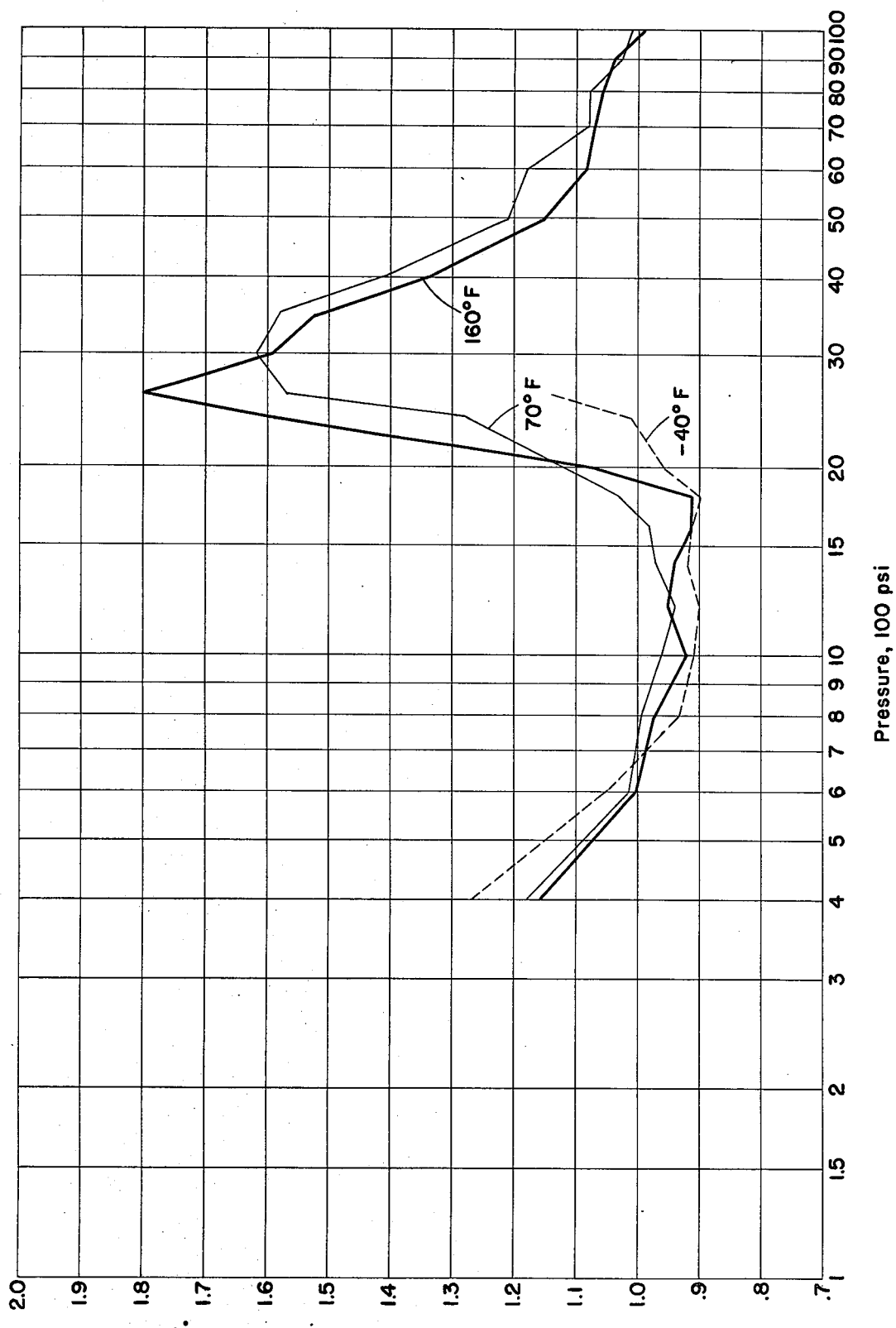

As in Example VII, a comparable propellant composition not containing the modifier according to this invention was prepared, and the modifier activity (B/Bo) determined over the same range of temperatures and pressures. The results of these determinations are plotted graphically in FIG. 4. As shown in FIG. 4, the modifier activity was again appreciable in two distinct pressure regions, namely a low-pressure region in the neighborhood of 400 psi, and a high-pressure region where the maximum activity was observed in the range between 2,400 and 3,500 psi, and decreasing activity with increasing pressure over the whole range up to about 10,000 psi.

Taking FIG. 3 into consideration together with FIG. 4, it is evident that the normal tendency for burning rate to increase with increasing pressure was offset by a simultaneous decrease in modifier activity throughout the range between 2,500 and 5,000 psi, after which the tendency for burning rate to increase was so great that it could no longer be offset by the decrease in modifier activity.

Comparing FIG. 2, with FIG. 4, it will be noted that the modifier activity in the high-pressure region was even greater in the composition of Example VIII, which had a relatively high heat of explosion amounting to 998 cal./gm., than in the composition of Example VII, which had a relatively low heat of explosion amounting to only 864 cal./gm. This is in marked contrast to the behavior of conventional modifiers which, as noted above, tend to lose activity as the heat of explosion is increased.

The composition set forth in Example VII is a typical formulation designed for a nominal energy content, or heat of explosion, of 825 calories per gram, while that in Example VIII is a typical formulation designed for a nominal heat of explosion of 1000 calories per gram. Some degree of variation is possible in these formulations, but the permissable latitude for variation is generally small in view of other requirements for physical properties and the like, as will be understood to those skilled in the art. In the examples which follow, the compositions designated as having heats of explosion of 825 calories per gram were based upon the formulation of Example VII, while those designated as having heats of explosion of 1000 calories per gram were based upon the formulation of Example VIII.

With respect to the amount of modifier employed, the most common practice is to use approximately 2% of the modifier, although for some purposes, amounts as low as 0.5%, or as high as 5% or more, may be employed. In all of the following examples, the amount of modifier was kept uniform at 2% of the composition. All percentages mentioned herein, unless otherwise specified, are percentages by weight.

EXAMPLES IX-XLI

The lead chelate complexes of a number of ligands were prepared accoding to the methods hereinbefore described, and the complexes were incorporated into propellant compositions as modifiers therefore. Each of the complexes was incorporated into a propellant prepared according to the basic formulation given in Example VII (825 calories per gram) and also into a propellant prepared according to the formulation of Example VIII (1000 calories per gram). Except as indicated by the blanks in the table, each of the resulting propellant compositions was tested for burning rate at both high and low pressure, and the burning rate compared with that of an unmodified propellant tested under the same conditions. The results are set forth in Table I:

TABLE I

| BALLISTIC MODIFIER ACTIVITY - BURNING RATE RATIO AT 70° F. | | | | |
|---|---|---|---|---|
| | 825 CAL./GM. | | 1000 CAL./GM. | |
| LEAD COMPOUND OF | LOW PRESSURE | HIGH PRESSURE | LOW PRESSURE | HIGH PRESSURE |
| 9. SALICYLALDEHYDE | 2.48+ | 1.54 | 1.18+ | 1.62 |
| 10. 3-NITROSALICYLALDEHYDE | 1.88+ | — | 1.14+ | 1.13 |
| 11. 5-NITROSALICYLALDEHYDE | 1.37+ | 0.72 | 1.13+ | 1.11 |
| 12. 5-CHLOROSALICYLALDEHYDE | 1.74+ | 1.08 | 1.11+ | 1.37 |
| 13. 4,6-DIMETHYLSALICYLALDEHYDE | 1.65 | — | 1.19+ | 1.19 |
| 14. DIPHENYL LEAD SALICYLALDEHYDE | 2.13 | 1.17 | 1.285+ | 1.21 |
| 15. 3-CHLOROSALICYLALDEHYDE | 1.54+ | 1.15 | — | 1.17 |
| 16. 5-METHYLSALICYLALDEHYDE | 1.43+ | 1.71 | 1.07+ | 1.28 |
| 17. 5-t-BUTYLSALICYLALDEHYDE | 1.75 | 1.07 | 1.33+ | 1.31 |
| 18. 4-METHOXYSALICYLALDEHYDE | 1.56+ | 1.09 | 1.19+ | 1.20 |
| 19. 4-HYDROXYSALICYLALDEHYDE | 2.4 | 1.11 | 1.54+ | 1.31 |
| 20. 3-METHOXYSALICYLALDEHYDE | 2.21+ | 1.11 | 1.13+ | 1.21 |
| 21. 2,4-DIHYDROXYBENZOPHENONE | 1.82 | 1.225+ | 1.11+ | 1.21+ |
| 22. O-HYDROXYACETOPHENONE | 1.51+ | 1.13 | 1.0+ | 1.16 |
| 23. 2,5-DIHYDROXYBENZOQUINONE | 1.52 | 0.85 | 1.04+ | 1.05 |

TABLE I-continued

BALLISTIC MODIFIER ACTIVITY - BURNING RATE RATIO AT 70° F.

| | 825 CAL./GM. | | 1000 CAL./GM. | |
|---|---|---|---|---|
| LEAD COMPOUND OF | LOW PRESSURE | HIGH PRESSURE | LOW PRESSURE | HIGH PRESSURE |
| 24. BIS-O-HYDROXYPHENACYLPHENONE | 1.59 | — | 1.33 | 1.43 |
| 25. 2-HYDROXY-4-METHOXYBENZOPHENONE | 1.61+ | 1.17 | 1.215+ | 1.37 |
| 26. PHENYLSALICYLATE | 2.46+ | 1.1 | 1.45 | 1.14 |
| 27. ETHYLSALICYLATE | 2.17+ | 1.14+ | 1.3+ | 1.0+ |
| 28. DISALICYLAMIDE | 1.83 | 1.24 | 1.35+ | 1.17 |
| 29. DISALICYLETHYLENE DIAMIDE | 1.97+ | 1.11 | 1.36+ | 1.07 |
| 30. SALICYLAMIDE | 2.46+ | — | 1.54+ | 1.2+ |
| 31. BIS-SALICYLALDEHYDE-O-PHENYLENEDIIMINE | 2.03 | — | 1.48+ | 1.23 |
| 32. SALICYLIDENE ACETAMIDE | 1.365+ | 1.21 | 1.0+ | 0.97+ |
| 33. SALICYLALDOXIME | 2.3 | 1.15 | 1.31+ | 1.35 |
| 34. SALICYLALDEHYDE ETHYLENEDIIMINE | 2.19 | 1.19 | 1.45+ | 1.33 |
| 35. (O-CARBOXYPHENYL) SALICULALDIMINE | 1.65+ | 1.11 | 1.24+ | 1.26 |
| 36. N-(2-HYDROXYETHYL)-SALICYLALDIMINE | 2.67 | 1.58 | 1.275 | 1.47 |
| 37. O-NITROPHENOL | 2.79 | — | 1.07 | 1.37 |
| 38. 2-HYDROXYNAPTHALDEHYDE-1 | 2.3+ | 1.18 | 1.31 | 1.26 |
| 39. O-NITRONAPHTHOL-1 | 2.35 | 1.26 | 1.38 | 1.59 |
| 40. SALIGENIN | 2.48 | 1.12 | 1.54 | 1.33 |
| 41. DISALICYLIDENE ACETONE | 1.66 | — | 1.3+ | 1.10 |

In the above table the "low pressure region" designates pressures less than 2000 psig, and the "high pressure region" designates pressures greater than 2000 psig. The "burning rate ratio" is defined as:

$$\frac{\text{burning rate of modified propellant grain}}{\text{burning rate of basic (unmodified) matrix.}}$$

The above data set forth in Table 1 shows that, in propellant compositions formulated to a heat of explosion of 825 calories per gram, every one of the compounds of this invention had appreciable modifier activity, and in most cases very strong activity, in the low-pressure region, and almost every one of the compounds possessed good modifier activity in the high pressure region as well.

When incorporated into propellant compositions having heats of explosion of 1000 calories per gram, every one of the compounds tested had good modifier activity both in the low-pressure region and in the high-pressure region. In some cases, the activity (as expressed by the burning rate ratio) was even greater in the high-pressure region than in the low-pressure region.

The novel compounds of this invention are useful in a variety of ways, as their unique chemical nature will readily suggest to those skilled in the art. They have been described herein, however, with particular reference to their outstanding properties as modifiers for propellant compositions.

The propellant compositions according to this invention are admirably suited for a variety of applications, particularly in the field of propellants for ballistic missiles of various types.

While this invention has been described with reference to certain preferred embodiments and illustrated by way of specific examples, these are illustrative only, and the invention is not to be construed as limited, except as set forth in the appended claims.

I claim:

1. Lead chelate complex compounds selected from the group consisting of lead 3-nitrosalicylaldehyde, lead 5-nitrosalicylaldehyde, lead 5-chlorosalicylaldehyde, lead 2,4-dihydroxybenzophenone, lead ortho-hydroxyacetophenone, lead 1,4-dihydroxyanthraquinone, lead 2,5-dihydroxybenzoquinone, lead bis-ortho-hydroxyphenacylphenone, lead phenylsalicylate, lead ethylsalicylate, lead disalicylamide, lead disalicylethylene diamide, lead salicylamide, lead bis-salicylaldehyde-o-phenylene diimine, lead salicylidene acetamide, lead bis-salicylaldehydeethylene diimine, and lead (o-carboxyphenyl) salicylaldimine.

2. As a new chemical compound, lead 3-nitrosalicylaldehyde.

3. As a new chemical compound, lead 5-nitrosalicylaldehyde.

4. As a new chemical compound, lead 5-chlorosalicylaldehyde.

5. As a new chemical compound, lead 2,4-dihydroxybenzophenone.

6. As a new chemical compound, lead ortho-hydroxyacetophenone.

7. As a new chemical compound, lead 1,4-dihydroxyanthraquinone.

8. As a new chemical compound, lead 2,5-dihydroxybenzoquinone.

9. As a new chemical compound, lead bis-ortho-hydroxyphenacylphenone.

10. Lead phenylsalicylate.
11. Lead ethylsalicylate.
12. Lead disalicylamide.
13. Lead disalicylethylene diamide.
14. Lead salicylamide.
15. Lead bis-salicylaldehyde-o-phenylene diimine.
16. Lead salicylidene acetamide.
17. Lead bis-salicylaldehyde-ethylene diimine.
18. Lead (o-carboxyphenyl) salicylaldimine.

* * * * *